(12) United States Patent
Kuhtz et al.

(10) Patent No.: US 8,194,909 B2
(45) Date of Patent: Jun. 5, 2012

(54) EARPHONE, HEADSET AND EAR PROTECTOR

(75) Inventors: Jan Peter Kuhtz, Celle (DE); Olav Nisse, Hildesheim (DE)

(73) Assignee: Sennheiser electronic GmbH & Co. KG, Wedemark (DE)

( * ) Notice: Subject to any disclaimer, the term of this patent is extended or adjusted under 35 U.S.C. 154(b) by 768 days.

(21) Appl. No.: 12/334,207

(22) Filed: Dec. 12, 2008

(65) Prior Publication Data

US 2009/0154754 A1 Jun. 18, 2009

(30) Foreign Application Priority Data

Dec. 14, 2007 (DE) .......................... 10 2007 060 233

(51) Int. Cl.
*H04R 25/00* (2006.01)

(52) U.S. Cl. ........ 381/370; 381/371; 381/374; 381/379; 381/381; 2/209; 181/129

(58) Field of Classification Search .................. 381/370, 381/371, 374, 377, 378, 379, 381, 383; 2/209; 181/129

See application file for complete search history.

(56) References Cited

U.S. PATENT DOCUMENTS

| 1,579,412 | A | | 4/1926 | Stenberg |
| 2,886,818 | A | * | 5/1959 | Roberts ............................. 2/421 |
| 3,263,032 | A | | 7/1966 | Scanlon |
| 3,488,457 | A | | 1/1970 | Lahti |

FOREIGN PATENT DOCUMENTS

| DE | 3130059 | 4/1982 |
| JP | 2005-269075 | 9/2005 |

* cited by examiner

*Primary Examiner* — Ramon Barrera

(74) *Attorney, Agent, or Firm* — Kilpatrick Townsend & Stockton LLP

(57) ABSTRACT

There is provided an earphone comprising a hoop (1) with a first and a second pivot point (A0, B0) at least one end of the hoop (1). The earphone has at least one earpiece (3) for receiving at least one electroacoustic transducer. The earpiece (3) has a first and a second pivot point (A, B). The earphone further has a first coupling element (2) for coupling the first pivot point (A0) of the hoop (1) to the first pivot point (A) of the earpiece (3) and a second coupling element (4) for coupling the second pivot point (B0) of the hoop (1) to the second pivot point (B) of the earpiece (3).

9 Claims, 2 Drawing Sheets

EARPHONE, HEADSET AND EAR PROTECTOR

CROSS-REFERENCE TO RELATED APPLICATIONS

This claims priority of German Patent Application No. 102007060233.4, filed Dec. 14, 2007, the disclosure of which is herein incorporated by reference in its entirety.

The present invention concerns an earphone, a headset and an ear protector unit.

In the case of headphones, in-ear earphones or headsets (listening-talking fitments) it is desirable if the transducer housing bears securely against the head of a user.

In the case of earpieces of headphones or headsets it can happen that those earpieces slip off the head as the holding force has to be applied to a spherical head.

As general state of the art attention is directed to DE 31 30 059, U.S. Pat. No. 1,579,412, U.S. Pat. No. 3,263,032, U.S. Pat. No. 3,488,457 and JP 2005-269075.

Therefore an object of the present invention is to provide an earphone, a headset and an ear protector which permits a stable fit for the earpiece on the head of a wearer.

That object is attained by an earphone as set forth in claim 1, a headset as set forth in claim 5 and an ear protector as set forth in claim 9.

Accordingly there is provided an earphone with a hoop with a first and a second pivot point at least one end of the hoop. The earphone has at least one earpiece for receiving at least one electroacoustic transducer. The earpiece has a first and a second pivot point. The earphone further has a first coupling element for coupling the first pivot point of the hoop and the first pivot point of the earpiece and a second coupling element for coupling the second pivot point of the hoop to the second pivot point of the earpiece.

The configuration of the two pivot points of the hoop and the two pivot points of the earpiece means that the earpiece can be pivoted or turned with a rotary axis substantially perpendicularly to a plane defined by the hoop.

In accordance with an aspect of the present invention the rotary axes of the first and second pivot points on the hoop and the first and second pivot points on the earpiece are substantially perpendicular to a plane defined by the hoop.

In accordance with an aspect of the present invention the first and second pivot points of the hoop and the first and second pivot points of the earpiece are so arranged that an operative pivot point is displaced in the direction of the ear-side end of the earpiece.

In accordance with a further aspect of the present invention the first and second coupling elements are each in the form of a rocking arm.

For that purpose the suspension of the earpiece is improved and a displaced operative pivot point between the hoop and the earpiece is provided.

The invention also concerns a headset having a hoop with a first and a second pivot point at least one end of the hoop. The headset has at least one earpiece for receiving at least one electroacoustic transducer. The earpiece has a first and a second pivot point. The headset further has a first coupling element for coupling the first pivot point of the hoop and the first pivot point of the earpiece and a second coupling element for coupling the second pivot point of the hoop to the second pivot point of the earpiece.

The invention also concerns an ear protector unit having a hoop with a first and a second pivot point at least one end of the hoop. The ear protector unit further has two earpieces respectively having a first and a second pivot point. The first pivot point of the hoop is coupled to the first pivot point of the earpiece with a first coupling element. The second pivot point of the hoop is coupled to the second pivot point of the earpiece with a second coupling element.

The above-described aspects of the present invention can also be used in relation to a headset in accordance with the present invention or an ear protector unit in accordance with the present invention.

The invention concerns the notion of displacing the pivot point between the hoop and the earpiece by way of a coupling transmission or a dual rocking arm to closely in front of, at or into the head in order to be able to provide for an improved action of force on the desired position.

In that way it is possible to permit a stable fit for the earphone or the headset on the head.

Further configurations of the invention are subject-matter of the appendant claims.

Embodiments and advantages of the invention are described in greater detail hereinafter with reference to the drawing.

Figure 1:
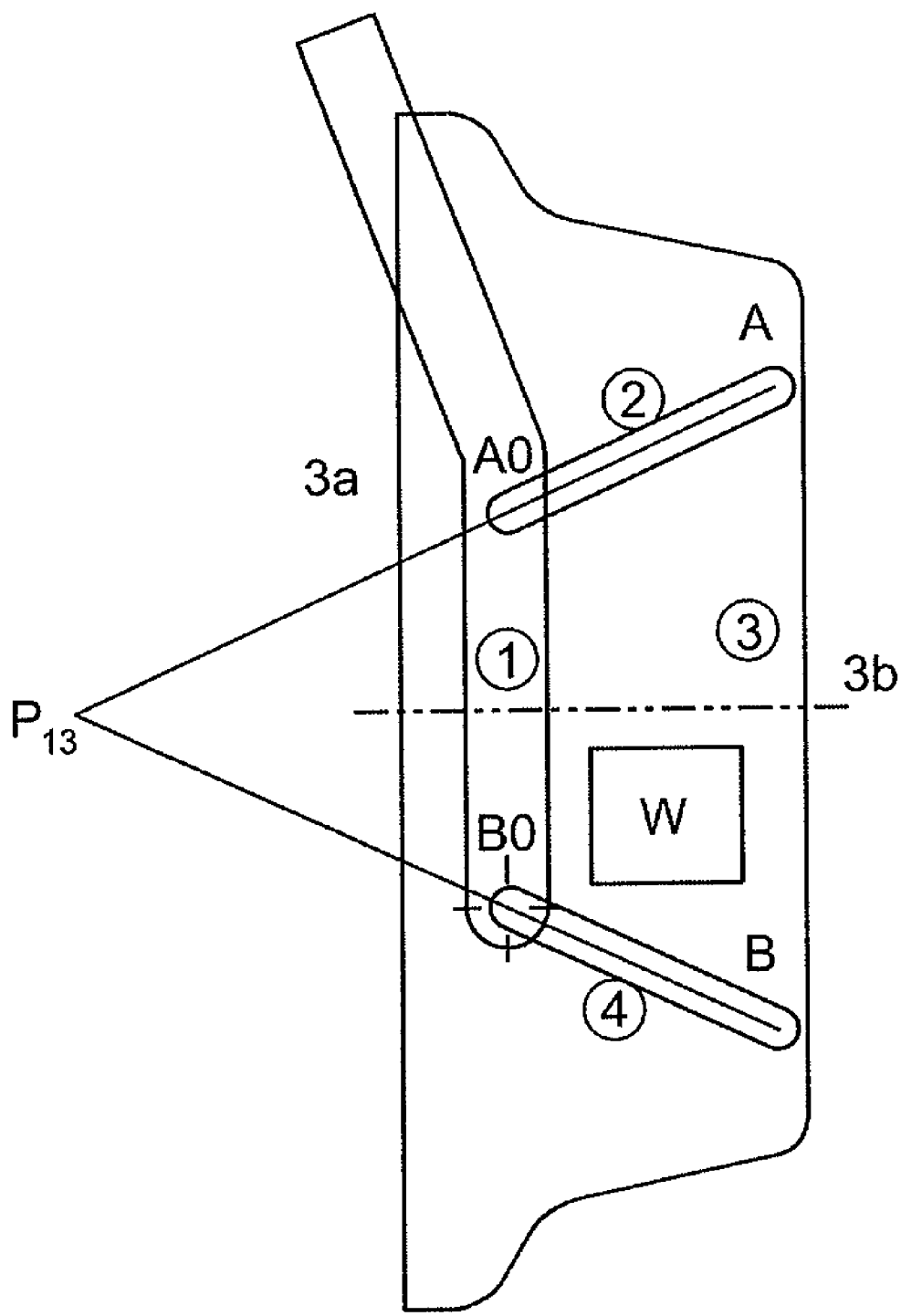
FIG. 1 shows a diagrammatic view in section in the region of the earpiece suspension configuration for an earphone in accordance with an embodiment of the invention.

FIG. 1 shows a diagrammatic view in section in the region of the earpiece suspension configuration of an earphone in accordance with an embodiment by way of example of the invention. The headphone or the headset in accordance with the first embodiment has a strap or hoop 1, at least one earpiece 3 (with an electroacoustic transducer W) and a first and a second rocking arm 2, 4 for each respective earpiece. A first and a second pivot point A0 and B0 are provided at the end of the hoop 1 which can be in the form of a fork. The earpiece 3 also has a first and a second pivot point A and B, wherein the pivot points A0 and A are connected together by way of the first rocking arm 2 and the pivot points B and B0 are connected together by way of the rocking arm 4. That can thus permit a coupling transmission involving a double rocking arm. The configuration of the headphone, shown in FIG. 1, permits a displaced operative pivot point between the fork/hoop and the earpiece 3. The displaced operative pivot point is denoted by $P_{13}$.

The first and second pivot points A, B of the earpiece 3 are provided in the region 3b of the earpiece, being the region that is away from the ear. The first and second pivot points A0, B0 of the hoop are arranged in the region 3a of the earpiece 3, being the region that is towards the ear. It is possible in that way to provide that the pivot point $P_{13}$ between the hoop 1 and the earpiece 3 is displaced to closely in front of, at or in the head. That is effected for example by a coupling transmission configuration, preferably in the form of a double rocking arm. The earpiece in accordance with the first embodiment can be of a design which embraces the ear or bears against the ear.

Figure 2:
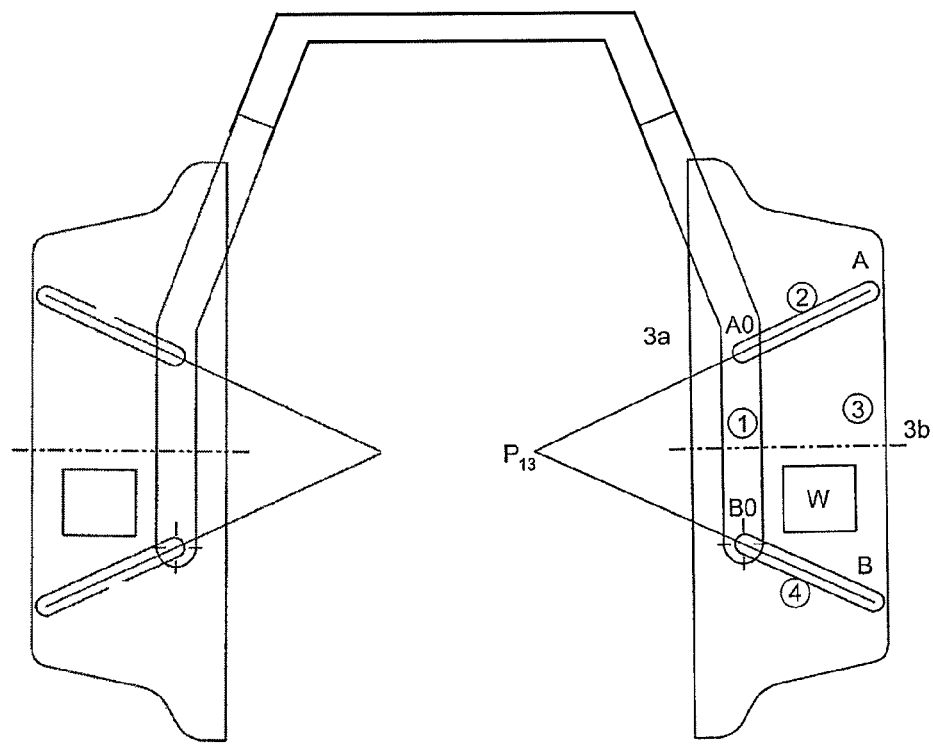
FIG. 2 shows a diagrammatic view in section in the region of a two earpiece suspension configuration for an earphone in accordance with an embodiment of the invention.

In accordance with a second embodiment the invention also concerns an ear protector comprising a hoop and two earpieces. The ends of the hoop can be connected together by way of the transmission configuration shown in FIG. 1, with the dual rocking arm arrangement. The (passive) ear protector unit thus substantially corresponds to the headphone of the first embodiment, but in this case the passive ear protector unit does not have an electroacoustic transducer. The earpiece in accordance with the second embodiment can completely enclose the ears of the wearer to ensure effective ear protection. The ear protector in accordance with the second embodiment can also be in the form of an active ear protector arrangement, as shown in FIG. 2, wherein at least one microphone, an active noise compensation unit and at least one electroacoustic reproduction transducer is provide in or on the ear protector.

The above-described rocking arms can be used as coupling elements. The coupling elements can be adapted to be adjustable (in their longitudinal direction).

The coupling elements can have a spring element. The above-described transmission arrangement between the earpiece and the end of the hoop has at least four members.

In accordance with the invention the rotary axes of the two pivot points at the end of the hoop and the rotary axes of the pivot points of the earpiece can be substantially perpendicular to a plane defined by the hoop 1.

In accordance with the invention the two pivot points A, B of the earpiece 3 can be provided at the side 3b or the end 3b of the earpiece, that is away from the ear. The end of the hoop 1 can preferably be arranged in accordance with the invention at the end 3a of the earpiece, that is towards the ear.

The invention claimed is:

1. An earphone comprising
a hoop having a first and a second pivot point on at least one end of the hoop, wherein the hoop defines a first plane, and wherein the first and second pivot points of the hoop each have a respective rotary axis substantially perpendicular to the plane defined by the hoop;
at least one earpiece having a first and a second pivot point for receiving at least one electroacoustic transducer, wherein the first and second pivot points of the earpiece each have a respective rotary axis perpendicular to the plane defined by the hoop;
a first coupling element for coupling the first pivot point of the hoop to the first pivot point of the earpiece; and
a second coupling element for coupling the second pivot point of the hoop to the second pivot point of the earpiece.

2. An earphone as set forth in claim 1 the first and second coupling elements are in the form of a rocking arm.

3. An earphone comprising:
a hoop having a first and a second pivot point on at least one end of the hoop;
at least one earpiece having a first and a second pivot point for receiving at least one electroacoustic transducer;
a first coupling element for coupling the first pivot point of the hoop to the first pivot point of the earpiece; and
a second coupling element for coupling the second pivot point of the hoop to the second pivot point of the earpiece, wherein the first and second pivot points of the hoop and the first and second pivot points of the earpiece are so arranged that an operative pivot point is displaced in the direction of an ear-side end of the earpiece.

4. A headset comprising;
a hoop having a first and a second pivot point on at least one end, wherein the hoop defines a first plane, and wherein the first and second pivot points of the hoop each have a respective rotary axis substantially perpendicular to the plane defined by the hoop;
at least one earpiece having a first and a second pivot point for receiving at least one electroacoustic transducer, wherein the first and second pivot points of the earpiece each have a respective rotary axis perpendicular to the plane defined by the hoop,
a first coupling element for coupling the first pivot point of the hoop to the first pivot point of the earpiece, and
a second coupling element for coupling the second pivot point of the hoop to the second pivot point of the earpiece.

5. A headset as set forth in claim 4 wherein the first and second coupling elements are in the form of a rocking arm.

6. A headset comprising;
a hoop having a first and a second pivot point on at least one end;
at least one earpiece having a first and a second pivot point for receiving at least one electroacoustic transducer,
a first coupling element for coupling the first pivot point of the hoop to the first pivot point of the earpiece, and
a second coupling element for coupling the second pivot point of the hoop to the second pivot point of the earpiece, wherein the first and second pivot points of the hoop and the first and second pivot points of the earpiece are so arranged that an operative pivot point is displaced in the direction of an ear-side end of the earpiece.

7. An ear protector unit comprising;
a hoop having a first and a second pivot point on at least one end of the hoop, wherein the hoop defines a first plane, wherein the first and second pivot points of the hoop each have a respective rotary axis perpendicular to the plane defined by the hoop;
two earpieces each having a respective first and second pivot point, wherein the first and second pivot points of each of the two earpieces have a respective rotary axis substantially perpendicular to the plane defined by the hoop;
a first coupling element for coupling the first pivot point of the hoop to the first pivot point of the earpiece; and
a second coupling element for coupling the second pivot point of the hoop to the second pivot point of the earpiece.

8. An ear protector unit comprising: a hoop having a first and a second pivot point on at least one end of the hoop; two earpieces each having a respective first and second pivot point; a first coupling element for coupling the first pivot point of the hoop to the first pivot point of the earpiece; and a second coupling element for coupling the second pivot point of the hoop to the second pivot point of the earpiece; wherein the first and second pivot points of the hoop and the first and second pivot points of the earpiece are so arranged that an operative pivot point is displaced in the direction of an earside end of the earpiece.

9. An ear protector unit as set forth in claim 7, wherein the two earpieces are adapted to enclose the ear.

* * * * *

UNITED STATES PATENT AND TRADEMARK OFFICE
CERTIFICATE OF CORRECTION

| | | |
|---|---|---|
| PATENT NO. | : 8,194,909 B2 | Page 1 of 1 |
| APPLICATION NO. | : 12/334207 | |
| DATED | : June 5, 2012 | |
| INVENTOR(S) | : Kuhtz et al. | |

It is certified that error appears in the above-identified patent and that said Letters Patent is hereby corrected as shown below:

<u>In the Abstract</u>:

Face page, second column, the second line of the ABSTRACT, section (57): please delete "at least" and insert --on at least--.

<u>In the Specification</u>:

In Column 1, Line 28, please delete "at least" and insert --on at least--.

In Column 1, Line 56, please delete "at least" and insert --on at least--.

In Column 1, Line 65, please delete "at least" and insert --on at least--.

In Column 2, Line 20, please delete "drawing" and insert --drawings--.

In Column 3, Line 3, please delete "is provide" and insert --is provided--.

<u>In the Claims</u>:

In Column 3, Line 40, please delete "the first" and insert --wherein the first--.

Signed and Sealed this
Eleventh Day of September, 2012

David J. Kappos
*Director of the United States Patent and Trademark Office*